United States Patent [19]

Röhrscheid et al.

[11] Patent Number: 5,523,472
[45] Date of Patent: Jun. 4, 1996

[54] PROCESS FOR THE PREPARATION OF 5-FLUOROANTHRANILIC ACID

[75] Inventors: Freimund Röhrscheid, Kelkheim; Jochen Rapp; Theodor Papenfuhs, both of Frankfurt, all of Germany

[73] Assignee: Hoechst Aktiengesellschaft, Frankfurt, Germany

[21] Appl. No.: 319,112

[22] Filed: Oct. 6, 1994

[30] Foreign Application Priority Data

Oct. 8, 1993 [DE] Germany ............. 43 34 431.3

[51] Int. Cl.⁶ ............. C07C 51/16; C07C 51/255; C07C 229/52; C07C 63/04
[52] U.S. Cl. ............. 562/408; 562/433; 562/456; 562/458; 562/493
[58] Field of Search ............. 562/456, 458, 562/408, 433, 456, 458, 493

[56] References Cited

U.S. PATENT DOCUMENTS 4,605,757 8/1986 Feld ............. 562/416
4,990,659 2/1991 Jihad et al. ............. 562/416

FOREIGN PATENT DOCUMENTS 0551632 7/1993 European Pat. Off. .
004200512A1 7/1993 Germany ............. C07C 25/02

OTHER PUBLICATIONS

European Search Report, Jan. 10, 1995, No. 94 11 4772.
J. Boil. Chem. Bd. 207, 1954—"Actionof some substituted Anthranilic Acids on *Escheria coli*".

*Primary Examiner*—José G. Dees
*Assistant Examiner*—Rosalynd A. Williams
*Attorney, Agent, or Firm*—Connolly and Hutz

[57] ABSTRACT

The present invention relates to a process for the preparation of 5-fluoroanthranilic acid, which comprises reacting 5-fluoro-2-bromotoluene in the presence of a catalyst and of an acidic solvent, with oxygen or an oxygen-containing gas at from 80° to 220° C., separating off the 5-fluoro-2-bromobenzoic acid formed and reacting it with ammonia at from 70° to 180° C.

38 Claims, No Drawings

PROCESS FOR THE PREPARATION OF 5-FLUOROANTHRANILIC ACID

DESCRIPTION

1. Field of the Invention

The present invention relates to a novel, advantageous process for the preparation of 5-fluoroanthranilic acid.

2. Description of the Prior Art

It is known that 5-fluoroanthranilic acid can be prepared by nitrating 3-fluorobenzoic acid and then reducing the 5-fluoro-2-nitrobenzoic acid formed (Rec. Trav. Chim. Pays-Bas 1914, 33, 336, Tetrahedron Lett. 1988, 29(40), 5105–8; J. Biol. Chem. 1954, 207, 411–2).

In this synthesis, during nitration, the isomeric 3-fluoro-2-nitrobenzoic acid is always formed but cannot be separated from the 5-fluoro-2-nitrobenzoic acid. The subsequent reduction of this product mixture, which contains about 2–3% 3-fluoro-2-nitrobenzoic acid, gives not only the desired product (5-fluoroanthranilic acid) but also to a corresponding extent 3-fluoroanthranilic acid which, however, cannot be separated from the 5-fluoroanthranilic acid.

DE-A 4 200 512 describes the preparation of haloanthranilic acids, in which an appropriate halo-2-bromobenzoic acid is reacted using aqueous ammonia and in the presence of a copper catalyst. Although the claimed process does indeed include a reaction of 5-fluoro-2-bromobenzoic acid to give 5-fluoroanthranilic acid, this preparation is supported neither by an example nor by indications of the yields and purities which can be obtained. Moreover, this synthesis is fairly difficult because of the preferred use of additional solvents and because of the use of copper compounds as catalyst, whose subsequent removal from the reaction product and the mother liquor is a highly complex technical procedure. The removal of the copper salts from the waste waters appears to be a particular problem, since the copper salts are present in complexed form. An indication of how these copper salts are to be removed from the waste waters is not given in DE-A 4 200 512.

The 5-fluoro-2-bromobenzoic acid which is required for the reaction with ammonia can be prepared by oxidation of 5-fluoro-2-bromotoluene using permanganate (J. Indian Chem. Soc. 1944, 21. 112–45 J. Org. Chem. 1988, 53(2), 345–52). This process, however, gives the desired product only in a yield of 70%. In addition, because the oxidation employs permanganate, the residues obtained contain considerable quantities of manganese. The disposal of such residues is difficult and requires a large outlay.

If the teaching of DE-A 4 200 512 is transferred to the preparation of 5-fluoroanthranilic acid, it becomes evident that the reaction of 5-fluoro-2-bromobenzoic acid with aqueous ammonia in the presence of a copper catalyst does not lead to the pure product desired. Rather, this process yields a 5-fluoroanthranilic acid which is heavily contaminated with 4,4'-difluorodiphenylamine-2,2'-dicarboxylic acid, and which cannot be purified further without an industrially unjustifiable expense. The corresponding experimental findings can be seen from Comparison Example 1.

Because 5-fluoroanthranilic acid is a valuable precursor in the preparation of pharmaceuticals (Czech Patent 159 570), herbicides (U.S. Pat. No. 3,905,800; EP 0 109 575; U.S. Pat. No. 4,388,472), plant growth regulators (FR 2 541 288) and fungicides of the quinazoline type (U.S. Pat. No. 4 824 469), the purity of this starting product is subject to stringent requirements.

There is therefore a considerable interest in rendering 5-fluoroanthranilic acid accessible in a technically simple way, in a high yield and with high purity. The object is at the same time to avoid the disadvantages described above.

SUMMARY OF THE INVENTION

This object is achieved by a novel process for the preparation of 5-fluoroanthranilic acid. It comprises reacting 5-fluoro-2-bromotoluene in the presence of a catalyst and of an acidic solvent with oxygen or an oxygen-containing gas at 80°–220° C., separating off the 5-fluoro-2-bromobenzoic acid formed and reacting it with ammonia at 70°–180° C.

The process according to the invention avoids the difficulties of the permanganate oxidation by reacting industrially available 5-fluoro-2-bromotoluene in a simple manner, by catalytic oxidation using oxygen or an oxygen-containing gas, with high yield and very good purity, to give 5-fluoro-2-bromobenzoic acid, without the need to take into account the production of residues containing manganese.

Furthermore, it has surprisingly been found that 5-fluoro-2-bromobenzoic acid can be reacted with ammonia, especially aqueous ammonia, without the addition of an organic solvent and without the addition of a copper catalyst, the reaction not only proceeding without problems but also providing the desired product in very high purity, avoiding unwanted secondary reactions. The 5-fluoroanthranilic acid prepared by this process is obtained in a purity which can be used without restrictions for the production of the above-mentioned biologically active substances.

5-Fluoro-2-bromotoluene is reacted with oxygen or an oxygen-containing gas in the presence of a catalyst which contains transition metal ions.

A highly suitable catalyst is a compound containing cobalt ions.

A particularly simple configuration of the process comprises the use of a catalyst which contains not only cobalt ions but also manganese ions. The use of a catalyst which contains bromide Ione as well as the transition metal ions has a positive effect on the reaction. It is recommended to use a catalyst which contains transition metal ions and bromide ions in a ratio of 1:(from 0.01 to 2), in particular 1:(from 0.1 to 1), preferably 1:(from 0.2 to 0.7).

If a catalyst is used which contains cobalt ions and manganese ions, then it is recommended to employ the cobalt ions and manganese ions in a ratio of 1:(from 0.01 to 3), in particular 1:(from 0.05 to 1).

It is generally adequate to employ the catalyst in a quantity corresponding to from 0.002 to 0.1 mol, in particular from 0.003 to 0.03 and preferably from 0.005 to 0.015 mol of transition metal ions per mole of 5-fluoro-2-bromotoluene.

The reaction is carried out in the presence of an acidic solvent. An aliphatic carboxylic acid having 1–8, in particular 2–6, carbon atoms is usually used as acidic solvent. However, it is also possible to use mixtures of these carboxylic acids. Highly suited acidic solvents are acetic acid, propionic acid, n-butyric acid and isoburytic acid, and mixtures thereof. A particularly simple configuration of the process comprises employing acetic acid and/or propionic acid as acidic solvent. In a number of cases acetic acid proves to be a particularly suitable acidic solvent.

The acidic solvent is usually employed in anhydrous form. During the reaction of 5-fluoro-2-bromotoluene with oxygen or the oxygen-containing gas, it should be ensured that the reaction mixture does not contain more than 15% by weight of water. Although a higher content of water does not hinder the reaction, it leads to a reduction in the reaction rate. It is particularly advantageous to limit the water content of the reaction mixture, during the reaction of 5-fluoro-2-bromotoluene, to a level of not more than 5% by weight.

The water content of the reaction mixture can be controlled by distilling off water from the reaction mixture, continuously or discontinuously.

The oxidation of 5-fluoro-2-bromotoluene can be carried out using pure oxygen or with an oxygen-containing gas. A particularly highly suitable oxygen-containing gas is air, especially dry air. As already mentioned above, the oxidation is usually carried out at a temperature of 80°–220° C.

In many cases it is adequate to carry out the oxidation at 130°–180° C., in particular 135°–160° C.

When the oxidation has ended the 5-fluoro-2-bromobenzoic acid formed is separated off, for example by filtration or centrifugation, and the resulting filtrate is freed by distillation from the water which, on the one hand, forms during the reaction and, on the other hand, may get into the reaction product because of the use of water-containing starting materials.

A favorable effect may be exerted on the oxidation by applying an oxygen partial pressure of at least 0.15 MPa, in particular 0.25 MPa and preferably 0.4 MPa, measured at the point of entry of the oxygen into the liquid phase. The transition metal ions are preferably added in the form of salts with carboxylic acids. The bromide ions can be added in the form of an HBr solution or as Potassium bromide, sodium bromide, cobalt bromide or manganese bromide.

The 5-fluoro-2-bromobenzoic acid crystallizes out of the reaction mixture obtained in the oxidation, with cooling if desired, and is separated off conventionally by filtration. However, since the filtrate contains the catalyst and considerable quantities of the desired product in solution, it is recommended to distill the filtrate on a column to remove the water it contains and to reuse the bottom product—the concentrated mother liquor containing the catalyst and the acidic solvent—as the reaction medium for the oxidation. The mother liquor can readily be reused in the oxidation up to 10 times or more before it requires separation by distillation into acidic solvent, which can be reused, and a residue which is suitable for landfill.

A further great advantage of the process according to the invention over the prior art is that the filtrate freed from water (mother liquor) can be reused as the reaction medium for the oxidation, whereas the permanganate oxidation only produces a waste water which is heavily contaminated with manganese and is difficult to dispose of.

The 5-fluoro-2-bromobenzoic acid is then reacted with ammonia in the absence of a catalyst. It is particularly simple to use ammonia in the form of an aqueous solution. The concentration of the aqueous solution containing ammonia is usually 20–50% by weight, in particular 25–33% by weight.

As already mentioned above, the reaction with ammonia is conventionally carried out at 70°–180° C. In many cases it is sufficient to carry out the reaction with ammonia at 90°–150° C., in particular 100°–130° C.

The reaction can be carried out at atmospheric pressure. However, the process is simplified by employing pressure. In general, it is sufficient to work at a pressure of 0.2–2.5 MPa, in particular 0.3–1.5 MPa and preferably 0.5–1.2 MPa. However, it is also possible to work at higher pressures, although this generally necessitates the use of suitable pressure apparatus.

In general, ammonia is employed in excess relative to the stoichiometric quantity required for the reaction, namely 3 mole-equivalents per mole of 5-fluoro-2-bromobenzoic acid. In most cases a ratio of 8–10 mole of ammonia per mole of 5-fluoro-2-bromobenzoic acid proves to be adequate. The amount of ammonia required by stoichiometry can be reduced by a third if the 5-fluoro-2-bromobenzoic acid is employed in the form of its salts, in particular its alkali metal salts or their aqueous solutions. If aqueous solutions of alkali metal salts of 5-fluoro-2-bromobenzoic acid are employed, then it should be ensured that the ammonia concentration in the reaction mixture is 20–50% by weight, preferably 25–33% by weight. This may necessitate the use of more highly concentrated aqueous ammonia solutions or of pure ammonia.

The reaction can be carried out batchwise by placing all of the reactants together at room temperature and then carrying out the reaction. A highly favorable procedure is one in which the initial charge is an aqueous ammonia solution, preheated to reaction temperature, and in which a solution of an ammonium salt and/or alkali metal salt of 5-fluoro-2-bromobenzoic acid in water is pumped in continuously, the reaction temperature being maintained by heating. After the end of the reaction, the reaction mixture is cooled, the apparatus is let down, and two mole-equivalents of alkali metal hydroxide, or only one mole-equivalent of alkali metal hydroxide in the case where alkali metal salts of 5-fluoro-2-bromobenzoic acid are employed, are added to the reaction mixture per mole of 5-fluoroanthranilic acid, and then excess ammonia is distilled off leaving an aqueous ammonia solution which can be reused.

The resulting alkali metal salt solution of 5-fluoroanthranilic acid can be precipitated by neutralization with aqueous mineral acid, for example aqueous hydrochloric or sulfuric acid, and the pure 5-fluoroanthranilic acid which precipitates can be isolated by filtration, washing with deionized water and drying at elevated temperature. A 5-fluoroanthranilic acid which is completely free from detectable impurities can be obtained by treating its acidic solution with active charcoal. For this purpose an already isolated 5-fluoroanthranilic acid can be used, but it is particularly simple to adjust the pH of the aqueous alkali metal salt solution of 5-fluoroanthranilic acid, as is present after the recovery of ammonia, to 0.5–1 using aqueous mineral acid, for example aqueous hydrochloric or sulfuric acid, and then to treat this solution with active charcoal and to neutralize the filtrate with alkali metal hydroxide. The 5-fluoroanthranilic acid obtained after filtration, washing and drying is of high purity (analytically pure).

The examples below describe the invention without limiting it.

EXAMPLES

Experimental Section

Example 1 (starting batch)

A solution of 2.99 parts of $Co(OAc)_2 \cdot 4H_2O$ 0.98 parts of $Mn(OAc)_2 \cdot 4H_2O$ 0.405 parts of HBr 302.4 parts of 5-fluoro-2-bromotoluene 330.0 parts of glacial acetic acid is placed in an autoclave and heated to 145° C., with stirring, at an $N_2$ pressure of 16 bar. Then air (16 bar) is passed in, the strongly exothermic reaction beginning immediately and consuming $O_2$. The temperature is adjusted to 160° C. The reaction is complete after 70 minutes. The homogeneous reaction solution is withdrawn from the autoclave at 100° C. and cooled with stirring.

The precipitated crystals are filtered off with strong suction, washed with 5×25 parts of 90% strength aqueous acetic acid, and dried.

Yield: 275.8 parts (78.7% of theory) of 5-fluoro-2-bromobenzoic acid

Melting point: 154–°155° C.

Purity: >99%

The concentration of the mother liquor to one quarter of its original volume provides an additional 35.0 parts (about 10% of theory) of 5-fluoro-2-bromobenzoic acid.

Examples 2–7 (subsequent batches)

The water and some of the acetic acid is removed by distillation from the mother liquor obtained, by analogy with Example 1, from the preceding batch in each case, to give 335 parts of a dewatered mother liquor to which 0.125 parts of Co $(OAc)_2 \cdot 4H_2O$, 0.049 parts of Mn $(OAc)_2 \cdot 4H_2O$ and 302.4 parts of 5-fluoro-2-bromotoluene are added, and this solution is oxidized and worked up in each case as described in Example 1. The resulting mother liquor, after dewatering and concentration to 335 parts, serves in each case as the initial charge for the next batch. A total of 5 mother-liquor recycling operations were carried out. The 5-fluoro-2-bromobenzoic acid obtained in all batches is of equivalent, reproducible quality (purity>99%).

Yield: (average of Examples 2–7):326.8 parts (93.3% of theory) of 5-fluoro-2-bromobenzoic acid Melting point: 152–°154° C.

Example 8

A mixture of 219 parts of 5-fluoro-2-bromobenzoic acid and 680 parts of 25% strength aqueous ammonia is heated for 2 hours in an autoclave at 140° C., a pressure of 1.0 MPa being established. The mixture is then cooled to 30° C., the autoclave is let down, and the excess ammonia is distilled off after the addition of 160 parts of 50% strength sodium hydroxide. The distillate obtained comprises 550 parts of 25% strength aqueous ammonia, which is used again in the next batch.

The resulting solution of sodium 5-fluoroanthranilate is adjusted to a pH of 0.5 using 670 parts of 15% strength hydrochloric acid, and, following the addition of 20 parts of active charcoal, is clarified at 95° C.

The filtrate is readjusted to a pH of 3.5 using 269 parts of 35% strength sodiumhydroxide and then cooled to 20° C., and the precipitate is filtered off with suction. After washing with deionized water and drying in vacuo at 100° C., 147 parts of 5-fluoroanthranilic acid are obtained, m.p. 182.5–°182.7° C., with a purity of 100% (HPLC). This corresponds to a yield of 95.0% of theory, based on the 5-fluoro-2-bromobenzoic acid employed. If the reaction is carried out for 5 hours at 110° C., an identical result is obtained.

Example 9

510 parts of 30% strength aqueous ammonia are heated at 130° C. in a closed autoclave, a pressure of 0.9 MPa being established. Then, over the course of 2 hours, an aqueous solution of sodium 5-fluoro-2-bromobenzoate, prepared from 219 parts of 5-fluoro-2-bromobenzoic acid and 240 parts of 16.7% strength aqueous sodium hydroxide, is pumped in continuously using a pressurized metering pump. The reaction temperature is maintained at 130° C. by gentle heating during the entire metering procedure, and stirring is carried out for 30 minutes at this temperature after the end of metering. The pressure rises only slightly during the reaction, to 0.95 MPa.

The mixture is then cooled, the autoclave is let down, and the excess ammonia is distilled off after 120 parts of 33% strength sodium hydroxide have been added, to produce a distillate comprising 500 parts of re-usable 25% strength aqueous ammonia.

After addition of 1500 parts of water, the solution of sodium 5-fluoroanthranilate (pH 9.5) is adjusted to a pH of 3.8 using 30% strength hydrochloric acid, the 5-fluoroanthranilic acid being precipitated in the form of colorless crystals. After cooling the mixture to 10° C. the crystals are filtered off with suction, washed with deionized water until salt-free and neutral, and dried to constant weight at 100° C. in vacuo.

151 parts of 5-fluoroanthranilic acid of m.p. 182–°182.5° C. are obtained with a purity of 99.8% (HPLC), corresponding to a yield of 97.2% of theory, based on 5-fluoro-2-bromobenzoic acid.

If the sodium salt solution of 5-fluoro-2-bromobenzoic acid is replaced by aliquot parts of the potassium or ammonium salt solution, prepared by dissolving 219 parts of 5-fluoro-2-bromobenzoic acid in 256.1 parts of 21.9% strength aqueous potassium hydroxide or, respectively, 217 parts of 7.9% aqueous ammonia solution and used as the metering medium in a procedure otherwise identical to that indicated, then 5-fluoroanthranilic acid is obtained in identical yield and quality.

A comparable result is also obtained by increasing the metering time to 4 hours and carrying out the reaction at 120° C.

Example 10

If the procedure of Example 9 is followed, but carrying out a clarification by charcoal in accordance with Example 8 after the distillation of the excess ammonia and after acidification of the 5-fluoroanthranilate solution to a pH of 0.5 and then working up the product as indicated in Example 8, 152 parts of 5-fluoroanthranilic acid of m.p. 182.6–°182.7° C. are obtained with a purity of 100% (HPLC), corresponding to a yield of 98.1% of theory, based on 5-fluoro-2-bromobenzoic acid.

Comparison Example 1

The amination of 5-fluoro-2-bromobenzoic acid in accordance with Example 5 (in conjunction with Example 1) of DE-A 4 200 512.

1.3 parts of copper(I) oxide in 69 parts of an aqueous, 25% strength ammonia solution are placed under nitrogen in a glass flask. A solution of 21.9 parts of 5-fluoro-2-bromobenzoic acid in 18 parts of 25% strength ammonia solution and 60 parts by volume of ethyl acetate are added to this initial charge over the course of 5 minutes, with stirring, at 25° C.

The reaction is carried out to completion under nitrogen. After addition of the ammonium benzoate solution, the reaction temperature rises to about 40° C. The copper(I) oxide suspension, which is initially reddish, changes to become a deep blue solution. After stirring for 1 hour at room temperature the reaction is complete. In order to complex the copper, 5.3 parts of ethylenediaminetetraacetic acid are added to the batch, which is then acidified with hydrochloric acid to a pH of 3.1, and the ethyl acetate is distilled off. The product is isolated at room temperature.

After filtration, washing with deionized water and drying in vacuo at 100° C., 14 parts of 5-fluoroanthranilic acid of m.p. 177°–177.5° C. are obtained with a purity of 92.7% (HPLC), corresponding to a yield of 83.7% of theory, based on the 5-fluoro-2-bromobenzoic acid employed.

By comparison with a pure substance (purity by HPLC: 99.8%, m.p. 281°–283° C.) synthesized independently by stoichiometric reaction of 5-fluoro-2-bromobenzoic acid with 5-fluoroanthranilic acid and caustic soda in dimethylacetamide, the principal impurity was identified as 4,4'-difluorodiphenylamine-2,2'-dicarboxylic acid, which was found to be present in a proportion of 7.1% (HPLC).

5-Fluoroanthranilic acid contaminated in this way is unsuitable for the production of the abovementioned pharmaceutical and agricultural active substances. It is not possible to purify it by recrystallization or reprecipitation.

Comparison Example 2

Amination according to the invention but in the presence of Cu salt

Example 9 is repeated precisely, the only difference being that one part of CuCl is added to the initial ammonia solution charge. After the 5-fluoro-2-bromobenzoate solution has been metered in and the batch worked up, 144 parts of 5-fluoroanthranilic acid of m.p. 176.5°–177.5° C. are obtained with a purity of 91.9% (HPLC), corresponding to a yield of 85.4% of theory, based on the 5-fluoro-2-bromobenzoic acid employed.

Analogously to Comparison Example 1, the principal impurity was identified as 4,4'-difluorodiphenylamine-2,2'-dicarboxylic acid and found to be present in a proportion of 7.6%. It was not possible to purify this by recrystallization or reprecipitation to give a product of suitable quality for production of the abovementioned pharmaceutical and agricultural active substances.

We claim:

1. A process for the preparation of 5-fluoroanthranilic acid, which comprises the steps of reacting 5-fluoro-2-bromo-toluene in the presence of a catalyst and of an acidic solvent, with oxygen or an oxygen-containing gas at from 80° to 220° C., separating off the 5-fluoro-2-bromobenzoic acid formed and reacting said 5-fluoro-2-bromobenzoic acid with ammonia at from 70° to 180° C. in the absence of a copper catalyst.

2. The process as claimed in claim 1, wherein the catalyst contains transition metal ions.

3. The process as claimed in claim 1, wherein the catalyst contains cobalt ions.

4. The process as claimed in claim 1, wherein the catalyst contains cobalt ions and manganese ions.

5. The process as claimed in claim 2, wherein the catalyst contains bromide ions in addition to the transition metal ions.

6. The process as claimed in claim 5, wherein the catalyst contains transition metal ions and bromide ions in a ratio of from 1.0.01 to 1.2.

7. The process as claimed in claim 4, wherein the catalyst contains cobalt ions and manganese ions in a ratio of from 1:0.01 to 1:3.

8. The process as claimed in claim 1, wherein the catalyst is employed in a quantity of from 0.002 to 0.1 mol of transition metal ions per mole of 5-fluoro-2-bromotoluene.

9. The process as claimed in claim 1, wherein the acidic solvent employed is an aliphatic carboxylic acid having 1 to 8 carbon atoms.

10. The process as claimed in claim 1, wherein the acidic solvent employed is acetic acid, propionic acid, n-butyric acid, isobutyric acid or mixtures thereof.

11. The process as claimed in claim 1, wherein the acidic solvent employed is acetic acid and/or propionic acid, especially acetic acid.

12. The process as claimed in claim 1, wherein during the reaction with oxygen or an oxygen-containing gas the reaction mixture contains up to 15% by weight of water.

13. The process as claimed in claim 1, wherein during the reaction with oxygen or an oxygen-containing gas the reaction mixture contains up to 5% by weight of water.

14. The process as claimed in claim 1, wherein the oxygen-containing gas employed is air.

15. The process as claimed in claim 1, wherein the reaction with oxygen or an oxygen-containing gas is carried out at from 130° to 180° C.

16. The process as claimed in claim 1, wherein an oxygen partial pressure of at least 0.15 MPa, measured at the point of entry into the liquid phase, is applied.

17. The process as claimed in claim 1, wherein the oxygen partial pressure of at least 0.25 MPa measured at the point of entry into the liquid phase, is applied.

18. The process as claimed in claim 1, wherein the 5-fluoro-2-bromobenzoic acid formed is separated off by filtration, and the resulting filtrate is freed from water by distillation and reused as the reaction medium.

19. The process as claimed in claim 1, wherein the 5-fluoro-2-bromobenzoic acid is reacted with an aqueous ammonia solution.

20. The process as claimed in claim 1, wherein the 5-fluoro-2-bromobenzoic acid is reacted with an aqueous ammonia-containing solution whose concentration is from 20 to 50% by weight.

21. The process as claimed in claim 1, wherein the reaction with ammonia is carried out at from 90° to 150° C.

22. The process as claimed in claim 1, wherein the reaction with ammonia is carried out at a pressure of from 0.2 to 2.5 MPa.

23. The process as claimed in claim 1, wherein the step of reacting said 5-fluoro-2-bromobenzoic acid with ammonia comprises passing 5-fluoro-2-bromobenzoic acid into a solution of an ammonium salt and/or an alkali metal salt of the 5-fluoro-2-bromobenzoic acid in water.

24. The process as claimed in claim 1, wherein the 5-fluoro-anthranilic acid thus formed in water is additionally treated with active charcoal, the active charcoal is filtered off, and alkali is added to the filtrate in order to precipitate 5-fluoroanthranilic acid.

25. The process as claimed in claim 6, wherein the catalyst contains transition metal ions and bromide ions in a ratio of from 1:0.1 to 1:1.

26. The process as claimed in claim 6, wherein the catalyst contains transition metal ions and bromide ions in a ratio of from 1:0.2 to 1:0.7.

27. The process as claimed in claim 7, wherein the catalyst contains cobalt ions and manganese ions in a ratio of from 1:0.05 to 1:1.

28. The process as claimed in claim 8, wherein the catalyst is employed in the quantity of from 0.003 to 0.03 mol of transition metal ions per mol of 5-fluoro-2-bromotoluene.

29. The process as claimed in claim 8, wherein the catalyst is employed in the quantity of from 0.005 to 0.015 mol of transition metal ions per mol of 5-fluoro-2-bromotoluene.

30. The process as claimed in claim 9, wherein the acidic solvent employed is an aliphatic carboxylic acid having from 2 to 6 carbon atoms.

31. The process as claimed in claim 14, wherein the oxygen-containing gas is dry air.

32. The process as claimed in claim 15, wherein the reaction with oxygen or an oxygen-containing gas is carried out at from 135° to 160° C.

33. The process as claimed in claim 17, wherein an oxygen partial pressure of at least 0.4 MPa, measured at the point of entry into the liquid phase, is applied.

34. The process as claimed in claim 20, wherein the 5-fluoro-2-bromobenzoic acid is reacted with an aqueous ammonia-containing solution whose concentration is from 25 to 33 % by weight.

35. The process as claimed in claim 21, wherein the reaction with ammonia is carried out at from 100° to 130° C.

36. The process as claimed in claim 22, wherein the reaction with ammonia is carried out at a pressure of from 0.3 to 1.5 MPa.

37. The process as claimed in claim 22, wherein the reaction with ammonia is carried out at a pressure of from 0.5 to 1.2 MPa.

38. A process for the preparation of 5-fluoroanthranilic acid, which comprises the steps of reacting 5-fluoro-2-bromotoluene in the presence of a catalyst and an anhydrous acidic solvent, with oxygen or an oxygen-containing gas at from 80° to 220° C., separating off the 5-fluoro-2-bromobenzoic acid formed, and, reacting the 5-fluoro-2-bromobenzoic acid thus formed with ammonia at from 70° to 180° C.

* * * * *

UNITED STATES PATENT AND TRADEMARK OFFICE
CERTIFICATE OF CORRECTION

PATENT NO. : 5,523,472
DATED : June 4, 1996
INVENTOR(S) : Freimund Röhrscheid, et al.

It is certified that error appears in the above-indentified patent and that said Letters Patent is hereby corrected as shown below:

Column 8, line 6, delete "1.0.01 to 1.2" and substitute

-- 1:0.01 to 1:2 --.

Signed and Sealed this

Eighth Day of October, 1996

Attest:

BRUCE LEHMAN

Attesting Officer     Commissioner of Patents and Trademarks